United States Patent
Ermakov et al.

(10) Patent No.: US 7,495,216 B2
(45) Date of Patent: Feb. 24, 2009

(54) ELECTRON BEAM APPARATUS FOR WORK FUNCTION MEASUREMENTS

(76) Inventors: Alexei Victorovich Ermakov, 610 Taylor Rd., Dept. of CCB, Piscataway, NJ (US) 08854; Barbara Jane Hinch, 610 Taylor Rd., Dept. of CCB, Piscataway, NJ (US) 08854

( * ) Notice: Subject to any disclaimer, the term of this patent is extended or adjusted under 35 U.S.C. 154(b) by 192 days.

(21) Appl. No.: 11/685,693

(22) Filed: Mar. 13, 2007

(65) Prior Publication Data
US 2008/0035845 A1  Feb. 14, 2008

Related U.S. Application Data

(60) Provisional application No. 60/781,338, filed on Mar. 13, 2006.

(51) Int. Cl.
*H01J 37/244* (2006.01)
*G01N 23/00* (2006.01)

(52) U.S. Cl. ............... 250/310; 250/306; 250/396 R; 250/397; 250/491.1; 250/492.2

(58) Field of Classification Search ........... 250/310, 250/306, 396 R, 491.1, 492.2, 397
See application file for complete search history.

(56) References Cited

U.S. PATENT DOCUMENTS 6,627,903 B1* 9/2003 Hirayanagi ............ 250/491.1
7,015,467 B2* 3/2006 Maldonado ............ 250/306

\* cited by examiner

*Primary Examiner*—Nikita Wells

(57) ABSTRACT

The inventive apparatus measures workfunction values using deflection of an electron beam without direct contact of the electron beam with the sample surface. The apparatus, mounted within a vacuum chamber, includes an electron gun, a position sensitive electron detector, and a sample. The sample is located such that an electron beam emanating from the gun can approach the surface and then be deflected into the position sensitive electron detector. Workfunction values are then derived from a measured deflected-electron position distribution.

14 Claims, 1 Drawing Sheet

ELECTRON BEAM APPARATUS FOR WORK FUNCTION MEASUREMENTS

STATEMENT REGARDING FEDERALLY SPONSORED RESEARCH OR DEVELOPMENT

The research and development for inventions described in this application received funding from NSF under Grant #CHE0313717. The U.S. Government may have certain rights in this invention.

BACKGROUND OF THE INVENTION

The invention pertains to methods and apparatus for performing measurements of surface contact potential (workfunction) changes of conductive samples during surface modification of (deposition of different materials or chemical reactions on) such samples.

For a variety of commercially and scientifically significant purposes it is desirable to perform workfunction measurements of a sample. For example, a workfunction value is very sensitive to deposition of different materials on the surface of the sample.

Surface potentials (or workfunctions) can be determined using Kelvin Probe methods. Kelvin Probe methods can provide higher accuracy than other existing methods, but the Kelvin Probe methods requires a vibrating electrode to be placed in close proximity to the surface of the sample. Therefore, Kelvin Probe methods cannot easily be used simultaneously with other sample characterization or modification techniques.

Other methods for workfunction measurements include electron beam current and photoemission methods. Those methods do not require any obstructive electrodes placed in close proximity to the surface of the sample. However, the surface of the sample is subjected to bombardment by electrons or energetic photons. In some cases primary electrons, secondary electrons or UV light may cause unwanted modification of the surface.

We have developed an entirely new method for workfunction measurements, which requires neither electrodes in close proximity to the sample surface, nor sample impinging electrons or UV photons.

SUMMARY OF THE INVENTION

The inventive apparatus is capable of performing workfunction measurements using deflection of an electron beam without direct contact of electron beam with the sample surface.

In preferred embodiment, the apparatus, mounted within a vacuum chamber, includes an electron gun, a position sensitive electron detector, and a sample having a surface. The sample is located such that an electron beam emanating from the gun can approach the surface and then be deflected into the position sensitive electron detector. Workfunction values are then derived from the measured position-sensitive electron distribution.

The apparatus also includes means for producing all necessary potentials for the electron gun, the sample and the position sensitive electron detector.

DETAILED DESCRIPTION OF THE INVENTION

Figure 1:
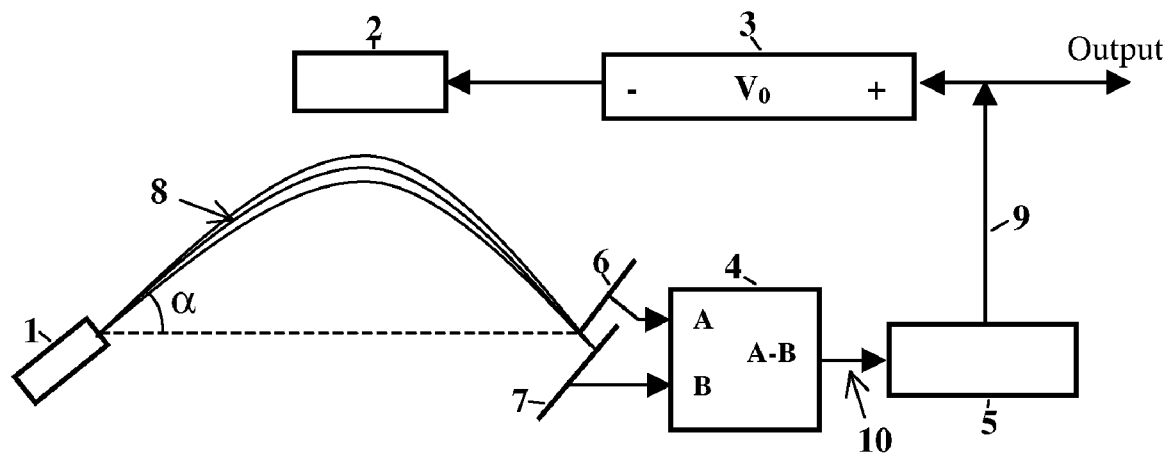
FIG. 1 Simplified schematic diagram of a preferred embodiment of the inventive apparatus. 1—electron gun, 2—sample, 3—bias power supply, 4—differential current amplifier, 5—integrator, 6, 7—detector plates, 8—electron beam.

In a preferred embodiment of our invention electrons from the electron gun 1, situated in front of a sample surface 2, as illustrated in FIG. 1, are deflected by an initial applied negative potential on the sample, $V_o$. The electron trajectories 8 are such that they are to be collected at the detector (6,7), which is located symmetrically in front of the plane of the surface. The detector comprises two overlapping conducting collector plates 6 and 7. The negative (electron) currents, collected by the two plates, are amplified by the differential amplifier 4, and the integrator 5 integrates a difference signal 10. The integrator output signal 9, is then applied to the "positive" end of the (fixed but) floating bias supply module 3. If the electron beam were not initially at the center of the detector, and the magnitude of the electron current from plate 6 was greater than that from plate 7, the difference signal 10, A-B, would be negative and the voltage of the integrator output signal 9, from the integrator 5, would continuously move towards more negative values. But the integrator output 9 is used to modify the applied sample potential, giving negative feedback on the difference signal, A-B. For the example above, the sample potential would be made more negative, deflecting the electron beam further towards plate 7, until the beam hits exactly centrally in the detector. The difference signal, A-B, then reaches zero and a stable electron trajectory is established. With this feedback the sample surface potential is then held constant, and all changes of the sample's work function are tracked by changes in the sample bias. The bias supply, at $V_o$, provides the large component of the necessary negative sample potential, $V_s$, allowing the output of the integrator 9 (the signal output) to be close to ground potential.

The electron gun 1 can be made from one of many well-established designs, similar to those used in oscilloscopes, CRT monitors and TV picture tubes. The bias power supply 3, the differential current amplifier 4, and the integrator 5 can be off-the-shelf commercially produced units or can be made specifically for this application using well-known circuit diagrams.

Figure 3:
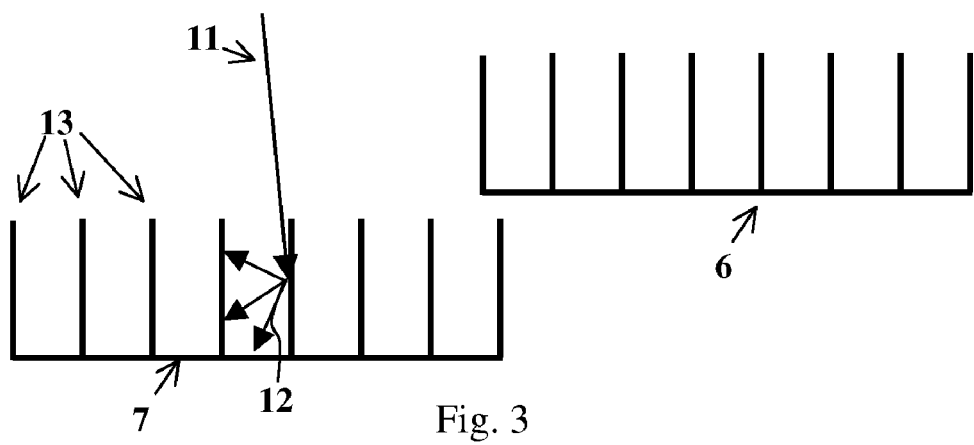
FIG. 3 A preferred detector design. 6, 7—detector plates, 13—high aspect ratio features, 11—primary electrons, 12—secondary electrons.

In order to reduce secondary electron emission from the detector plates, the surfaces of the conducting collector plates (6,7) can be covered with high aspect ratio features 13, as shown in FIG. 3. High aspect ratio features form so-called Faraday cups, which trap most of the secondary electrons 12 and therefore allow for more accurate measurement of the primary electron current. Primary, higher-energy, electrons 11 hit the sides of the high aspect ratio features 13 and produce lower-energy secondary electrons 12, which are absorbed by other high aspect ratio features 13.

Figure 2:
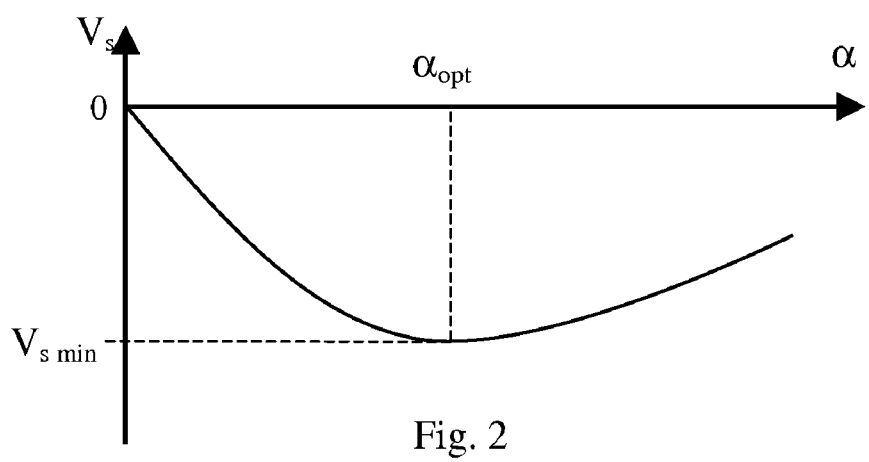
FIG. 2 Plot of the sample potential, required to deflect electrons to the center of the detector vs. the elevation angle $\alpha$.

The initial elevation angle $\alpha$ of an electron trajectory 8, see FIG. 1, is defined such that when $\alpha=0$ a straight electron trajectory goes directly from gun to detector plates 6,7 and, this trajectory is realized only when $V_s=0$, and the electrons do not experience external electric fields. More generally the electric field around the sample, experienced by the electrons, is non-uniform and its strength increases rapidly on approach to the sample 2. Thus the electrons with trajectories that are closer to the sample are deflected to a greater extent than the electrons with trajectories that are farther from the sample. FIG. 1 illustrates the fact that for a finite angular range of incident trajectories 8 the electron beam can be focused at the detector with one sample bias. However, as the angle of approach deviates from an optimum, $\alpha_{opt}$, the trajectories can be forced to reach the detector center only by changing the sample bias, and electric field strengths. In FIG. 2, a plot of sample potentials, $V_s$, required to deflect electrons to the center of the detector, we see that at small $\alpha$ the required sample potential becomes more negative as $\alpha$ increases. At much larger $\alpha$, electrons can more closely approach the sample surface, where the electric fields are stronger, and the sample potential needed to deflect electrons to the center of the detector again becomes less negative. At $\alpha_{opt}$ the required sample potential is most negative.

Operation at $V_s=V_{s\ min}$ and with $\alpha$ close to $\alpha_{opt}$ is optimal in two senses. It is at this condition that a divergent electron beam is focused at the detector. Absolute collected currents are maximized and fractional noise in the collected currents is minimized. It is also at the same condition that the measured output is least sensitive to small fluctuations of the initial e-beam incidence angle. This optimal condition can be achieved by means of scanning the initial intended beam elevation angle $\alpha$, and selecting an angle at which the output signal 9 has a minimum, i.e. has a most negative potential.

For most sensitivity to sample work function variations the electron beam trajectory 8 also should be aligned in a plane that includes the sample center. The angle of deflection of the electron beam, at fixed sample potential, is then maximized. Optimization of the "out of plane angle", perpendicular to $\alpha$, is best achieved with the following method. Using automatic feedback of the sample potential, thereby keeping the electron beam located equally between the detector plates (6,7), adjust the out of plane angle such that the sample potential and output signal (9) becomes least negative.

Summarizing the above optimal trajectory conditions we can state that, in order to enhance stability and reduce noise on the output signal, the signal 9 (whilst always negative) should be both maximized (least negative) by shifting the plane of the e-beam trajectory, and minimized (most negative) by varying the elevation angle $\alpha$ to $\alpha_{opt}$. With these optimal trajectories the electron gun itself can then be focused to minimize spot size at the detector plates, thereby further increasing the accuracy of the work function measurements.

We claim:

1. An apparatus for measurement of a sample surface work-function value, comprising:
   an electron beam source;
   a position sensitive electron detector; and
   a sample located such that an electron beam from said electron beam source deflects through an electron beam deflection angle to a said position sensitive electron detector without direct contact of the electron beam with the sample surface; and
   said workfunction value is derivable from a detected electron position signal.

2. An apparatus of claim 1 with sample bias adjustment means to change said electron beam deflection angle.

3. An apparatus of claim 2 with said sample bias adjustment means to simultaneously change said electron beam deflection angle, and to position and focus said electron beam within said position sensitive electron detector.

4. An apparatus of claim 1 with electron energy adjustment means of said electron beam source to change said electron beam deflection angle of said electron beam.

5. An apparatus of claim 4 with said electron energy adjustment means to simultaneously change said electron beam deflection angle, and to position and focus said electron beam within said position sensitive electron detector.

6. An apparatus of claim 1 with said position sensitive electron detector comprising two conductive electrodes separated across a line perpendicular to the plane containing said electron beam source said sample and said two conductive electrodes, thereby to generate said detected electron position signal from an electron current difference signal obtained by subtracting collected electron currents from said two conductive electrodes.

7. An apparatus of claim 6 with differential current amplifier using said collected electron currents to generate said electron current difference signal.

8. An apparatus of claim 6 with programmable sample bias means, and with integrator connected to said electron current difference signal and said programmable sample bias means, with integrator output of said integrator providing negative feedback on said electron beam deflection angle and allowing automatic sample potential tracking of all sample work function changes.

9. An apparatus of claim 8 with said programmable sample bias means comprising a low voltage programmable bias unit, and a higher voltage negative sample bias supply, thereby allowing said integrator output to be close to ground potential, and allowing use of said integrator output for direct sample work function measurement.

10. An apparatus of claim 8 in which by maximizing said integrator output said electron beam is directed into the plane containing: said sample, said electron beam source, and a desired position within said position sensitive electron detector.

11. An apparatus of claim 8 in which, by minimizing said integrator output, said electron beam is optimally directed within the plane containing: said sample, said electron beam source, and a desired position within said position sensitive electron detector.

12. An apparatus of claim 1 with said electron beam source having means for deflection of said electron beam.

13. An apparatus of claim 1 with said electron beam source having means for focusing of said electron beam.

14. An apparatus of claim 1 with said position sensitive electron detector comprising a minimum of two conductive Faraday cup design electrodes, thereby minimizing secondary electron emission current effects on said detected electron position signal from said minimum of two conductive Faraday cup design electrodes.

* * * * *